(12) United States Patent
Hurlin et al.

(10) Patent No.: US 9,943,892 B2
(45) Date of Patent: Apr. 17, 2018

(54) SYSTEM FOR THE CONTINUOUS TREATMENT OF PRODUCTS BY THERMAL INPUT

(71) Applicant: AMB, Mons (BE)

(72) Inventors: Gauthier Hurlin, Trith-St-leger (FR); Sebastien Corneillie, Peruwelz (BE)

(73) Assignee: AMB, Mons (BE)

( * ) Notice: Subject to any disclaimer, the term of this patent is extended or adjusted under 35 U.S.C. 154(b) by 0 days.

(21) Appl. No.: 15/327,574

(22) PCT Filed: Jul. 16, 2015

(86) PCT No.: PCT/EP2015/066240
§ 371 (c)(1),
(2) Date: Jan. 19, 2017

(87) PCT Pub. No.: WO2016/012334
PCT Pub. Date: Jan. 28, 2016

(65) Prior Publication Data
US 2017/0182531 A1    Jun. 29, 2017

(30) Foreign Application Priority Data

Jul. 22, 2014 (FR) .................................... 14 57081

(51) Int. Cl.
*B09B 3/00* (2006.01)
*A61L 11/00* (2006.01)
*H05B 6/78* (2006.01)

(52) U.S. Cl.
CPC ............ *B09B 3/0083* (2013.01); *A61L 11/00* (2013.01); *B09B 3/0075* (2013.01); *H05B 6/78* (2013.01); *H05B 2206/044* (2013.01); *H05B 2206/045* (2013.01)

(58) Field of Classification Search
CPC ....... B09B 3/00; B09B 3/0083; B09B 3/0075; A61L 11/00; H05B 6/78
USPC ......................................................... 588/321
See application file for complete search history.

(56) References Cited

U.S. PATENT DOCUMENTS

| 3,704,523 A | 12/1972 | Guerga et al. |
| 4,184,587 A | 1/1980 | Hallstrom |
| 2005/0238865 A1 | 10/2005 | Konishi |

FOREIGN PATENT DOCUMENTS

| DE | 35 05 570 C1 | 1/1991 |
| EP | 0 103 396 A2 | 3/1984 |
| EP | 0 334 460 A2 | 9/1989 |
| EP | 0 710 636 A1 | 5/1996 |
| FR | 2 646 083 A1 | 10/1990 |
| FR | 2 909 079 A1 | 5/2008 |
| FR | 2 982 510 A1 | 5/2013 |
| GB | 1 363 923 A | 8/1974 |

OTHER PUBLICATIONS

International Search Report, dated Oct. 12, 2015, from corresponding PCT application.

*Primary Examiner* — Edward Johnson
(74) *Attorney, Agent, or Firm* — Young & Thompson

(57) ABSTRACT

A system (21) for the continuous treatment of products such as waste by thermal input, includes: —a product treatment chamber (210), —a device (211) for supplying heat by microwave generators (211*a*), arranged with respect to the chamber (210) such that the microwaves are contained in the chamber (210), —a moving floor transportation device (212) resting on the bottom of the chamber (210), capable of transporting a layer of products (D) from the entry thereof into the chamber until the exit thereof from the chamber, —a containment device (213) for the products and the vapors released by same, inside the chamber.

20 Claims, 5 Drawing Sheets

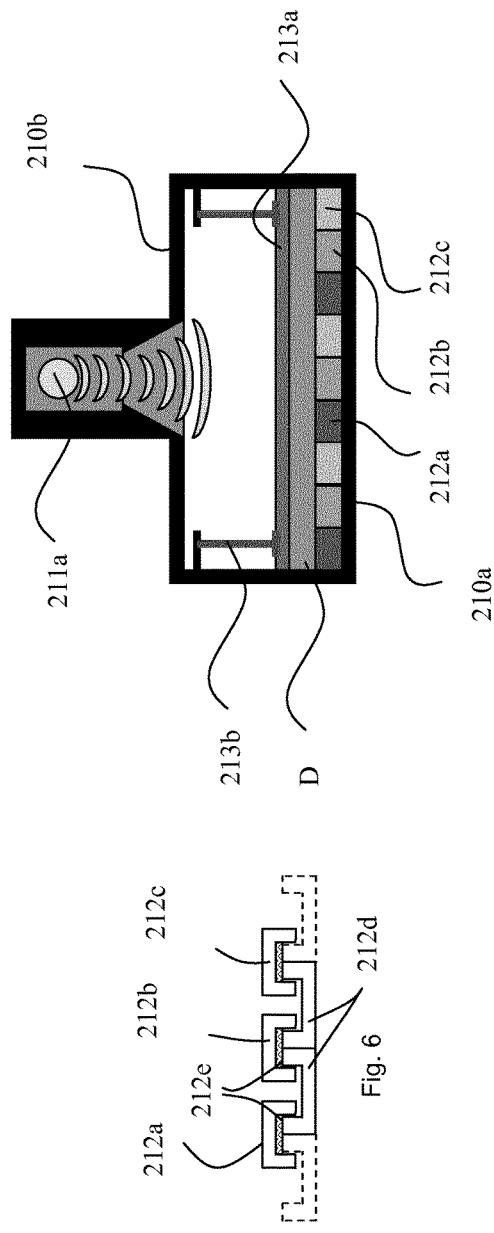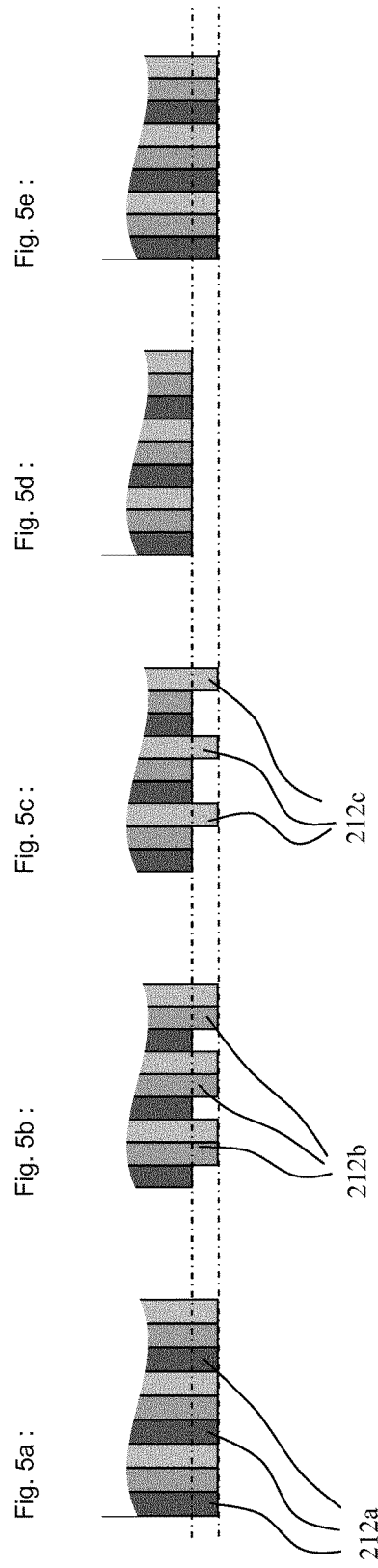

SYSTEM FOR THE CONTINUOUS TREATMENT OF PRODUCTS BY THERMAL INPUT

Figure 1:
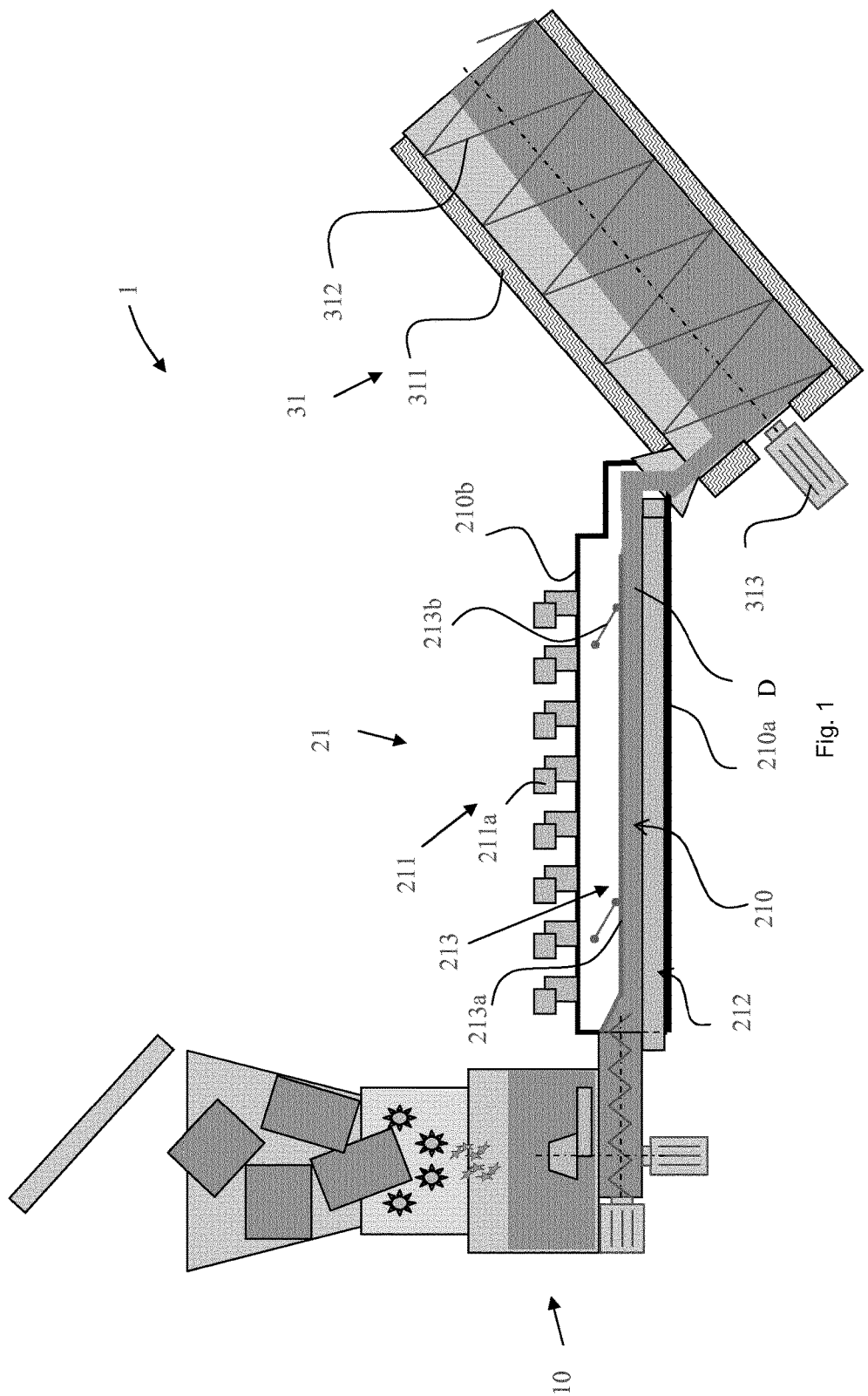

The invention relates to a system for the continuous treatment of products by thermal input. Such a system finds a particular, non-restrictive, application in a facility for the hygienisation or decontamination of waste.

The term hygienise denotes the act of reducing to acceptable levels pathogenic agent concentrations in waste. To this end, the waste is held in a temperature range greater than or equal to 70° C., which is typically between 70° C. and 75° C.

The term decontaminate denotes the act of destroying pathogenic agents in waste having an infectious risk such as medical waste. To this end, the waste is held in a temperature range greater than or equal to 100° C., typically between 100° C. and 110° C.

The prior art includes facilities for the treatment of waste having an infectious risk by microwaves, operating continuously, enabling the decontamination thereof. Conventionally, this type of continuous treatment facility comprises a first system shredding the waste, in the form of aggregates of sufficiently reduced size with regard to the legislation, a second heating system rapidly raising the aggregates to a temperature of approximately 100° C. for decontamination, and a third system holding, for a sufficient time, the aggregates at a temperature close to but greater than that reached in the second system, so as to decontaminate the waste.

As such, the document FR 2.646.083 describes a facility for the decontamination of medical waste corresponding to the general description stated in the preceding paragraph, wherein the second heating system implements a rise in the temperature of waste by means of microwaves in the chamber of a conduit receiving the screw of a transportation device, this transportation device moving the waste between the first system and the third system.

In order to ensure the penetration of the microwaves into the transportation device, it is necessary to restrict the diameter of the conduit forming the chamber of the device to some ten centimeters. This small diameter causes frequent blockages of the screw in the conduit, which gives rise to operating difficulties and losses of productivity.

The present applicant sought to solve this problem by proposing a facility (document FR 2.982.510) implementing a microwave treatment in a chamber surrounding a vibratory conveyor. Such a solution has the drawback of requiring, in order to confine the vapours and microwaves in the chamber, the presence of a dynamic seal between a fixed upper portion and a movable lower portion forming the treatment chamber. In practice, the use of such a dynamic seal proves to be complex and costly.

The document DE 35 05 570 C1 belongs to the field of the decontamination of infectious waste, and in particular hospital waste, and describes a facility intended for the decontamination of infectious waste. The infectious waste arrives via the belt conveyor and feeds a hopper. Once the door has been closed, a device is actuated and sprays water onto the waste, and the waste is then shredded by rollers. The shredded waste falls onto the belt of the conveyor and is transported via a microwave treatment chamber.

A stainless steel casing defines the walls of the microwave chamber inside which the radiation is contained. A second casing, plastic and inside the metal casing, has the function of containing the waste in a reduced volume of the metal-walled chamber. Microwave emitters are provided outside the plastic casing. Infrared sensors are rigidly connected to the cover of the plastic casing, protruding internally into the internal volume of the plastic casing in order to monitor the temperature of the products in the chamber.

According to the observations of the inventor, a first major flaw of the facility of this document originates from the use of a belt conveyor for transporting the products via the microwave treatment chamber, in that the waste may comprise products adhering to the surface of the conveyor belt. In such a case, the products adhering to the belt are conveyed continually from the top to the bottom of the conveyor during feeding, without ever being discharged, even when the conveyor is associated with a scraping lip at the outlet, supposed to detach the products from the belt, but which, in practice, proves to be insufficient.

For this reason, and in this field, it is conventional for those skilled in the art to use screw conveyors which do not have this flaw and as disclosed by the document FR 2.646.083. Also for this reason, and in the facility described in the document FR 2.982.510 of the present applicant, a vibratory conveyor solution has been chosen with the aim of addressing the two problems identified above, when the conveyor is a screw or belt conveyor, respectively.

In the continuous microwave treatment facility of the document FR 2.646.083 having a screw conveyor, that of the document DE 35 05 570C1 having a belt conveyor, or that of the document FR 2.982.510 having a vibratory conveyor, the confinement of the waste may indeed be enhanced by the presence of a plastic, inner, casing, intended to confine the waste, in a reduced volume of a metal container, the function whereof is to contain the microwaves. As such, the document DE 35 05 570 C1 discloses a plastic casing, inside a metal casing, wherein the walls define the microwave chamber. The intrinsic function of this inner plastic casing, referenced 15a, is that of confining the waste and vapours discharged in a reduced volume of the microwave chamber.

However, and according to the observations of the inventor, the confinement of the waste is not optimal in that there is necessarily an empty space between the top surface of the layer of products to be treated, and the cover of the plastic casing. Such an empty space can be seen, for example, in FIG. 1 of the document DE 35 05 570. According to the observations of the inventor, the plastic cover of the confinement casing is positioned by those skilled in the art at a distance from the top surface of the layer of waste, so as to avoid the presence of friction between the layer of products and this static cover wall which would impede the progression of the waste under the action of the conveyor, and would thus give rise to jamming.

The field of ceramic article manufacture further includes microwave treatment heating facilities. The document GB 1.363.923, or the document U.S. Pat. No. 3,704,523 disclose such facilities finding a particular application for drying the ceramic products formed.

In both cases, the facility comprises a belt conveyor, conveying products into a microwave treatment chamber. In both cases, the microwave treatment only commences after lowering a chamber structure, and until the contact thereof with the conveyor. As such, and in the document U.S. Pat. No. 3,704,523, the chamber structure referenced 11 is actuated by the cylinder referenced 6a, until the base of the chamber structure, referenced 18, comes into contact with the conveyor belt. In the document GB 1.363.923, the chamber structure is referenced 15 and is actuated by the cylinder referenced 11a until the base of the chamber structure, referenced 20, comes into contact with the belt of the conveyor. In both cases, the intended aim is that of forming a tight treatment chamber for ceramic products, prior to the implementation of the microwave treatment which is then necessarily carried out when the belt conveyor is stopped.

Such treatment facilities disclosed by the documents U.S. Pat. No. 3,704,523 or GB 1.363.923 are discontinuous treatment facilities in that the microwave treatment is only activated after lowering the chamber structure and thus stopping the conveyor, and unlike the microwave treatment systems of the documents DE 35 05 570 C1, FR 2.982.510 or FR 2.646.083 which carry out continuous treatment of the products in the treatment chamber, i.e. a microwave treatment of the products while said products are moved in the chamber by the conveyor.

The aim of the present invention is that of remedying the drawbacks cited above by proposing a continuous microwave treatment system, having a simplified design, not susceptible to the blockage phenomenon as encountered in screw conveyor treatment systems, and not susceptible to the problems of adherent and poorly discharged products, as encountered in belt conveyors.

A further aim of the present invention is that of proposing, at least according to one embodiment, a treatment system of enhanced performance, in particular, and according to the observations of the inventors, by superior product confinement.

Further aims and advantages will emerge in the course of the description hereinafter which is merely given by way of indication and which is not intended to limit same.

Such a system will find a particular, non-restrictive, application as a second system and/or third system of a product treatment facility, the general architecture whereof is described above in connection with the prior art.

In addition, the invention firstly relates to a system for the continuous treatment of waste by thermal input, for the hygienisation of waste or the decontamination of such waste having an infectious risk, comprising:
  a waste treatment chamber,
  a device for supplying heat by microwave generators, arranged with respect to said chamber such that the microwaves are contained in said chamber,
  a moving floor transportation device, resting on the bottom of the chamber, capable of transporting a layer of waste from the entry thereof into the chamber until the exit thereof from the chamber, comprising a set of slats arranged in parallel forming said floor, along with a system for controlling the slats according to an alternating movement, capable of transporting a layer of waste,
  a confinement device for the waste and the vapours released thereby, inside said chamber.

According to optional features of the invention, taken alone or in combination:
  said confinement device for the waste and vapours released thereby comprises a confinement plate, inside said chamber, intended to bear on the layer of products, movable with respect to a fixed portion of the facility;
  the confinement plate is arranged in said chamber between, on one hand, the microwave generators of said device for supplying heat by microwave generators and, on the other, the layer of products, said confinement plate being made of a microwave-permeable material such as polytetrafluoroethylene;
  said confinement plate is suspended from a fixed portion of the facility by a rocking lever system;
  the moving floor transportation device is formed by a set of slats consisting of at least three subassemblies, said slats being arranged in parallel, along with a system for the sequential control of the slats according to an alternating movement, and if applicable the system comprises a device for heating the set of slats so as to form a heating moving floor.

According to a further alternative, the confinement device of the waste and vapours released thereby comprises a belt conveyor, inside said chamber, said belt conveyor comprising a flexible belt, guided by rotary guiding cylinders, said flexible belt being intended to bear on the layer of waste.

Preferably, the belt conveyor is arranged in said chamber between, on one hand, the microwave generators of said device for supplying heat by microwave generators and, on the other, the layer of waste, said flexible belt being intended to be traversed by the microwaves and being made of a microwave-permeable material such as silicone.

The invention further relates to a facility for the continuous treatment of products, comprising, in series:
  a first system for shredding or mixing waste,
  a second system for the continuous treatment of waste by thermal input to raise the temperature of the products,
  a third system for holding the temperature of the waste.

According to the invention, the second system or the third system consists of a system for the continuous treatment of products, according to the invention. Optionally, the second system and the third system each consist essentially of a system according to the invention.

The invention will be understood more clearly on reading the following description accompanied by the appended drawings wherein:

FIG. 1 is a view of a facility according to the invention according to a first embodiment, comprising a system according to the invention as the second system for raising the temperature of the products, the third system for holding the temperature of the products comprising an endless screw type transportation device.

Figure 2:
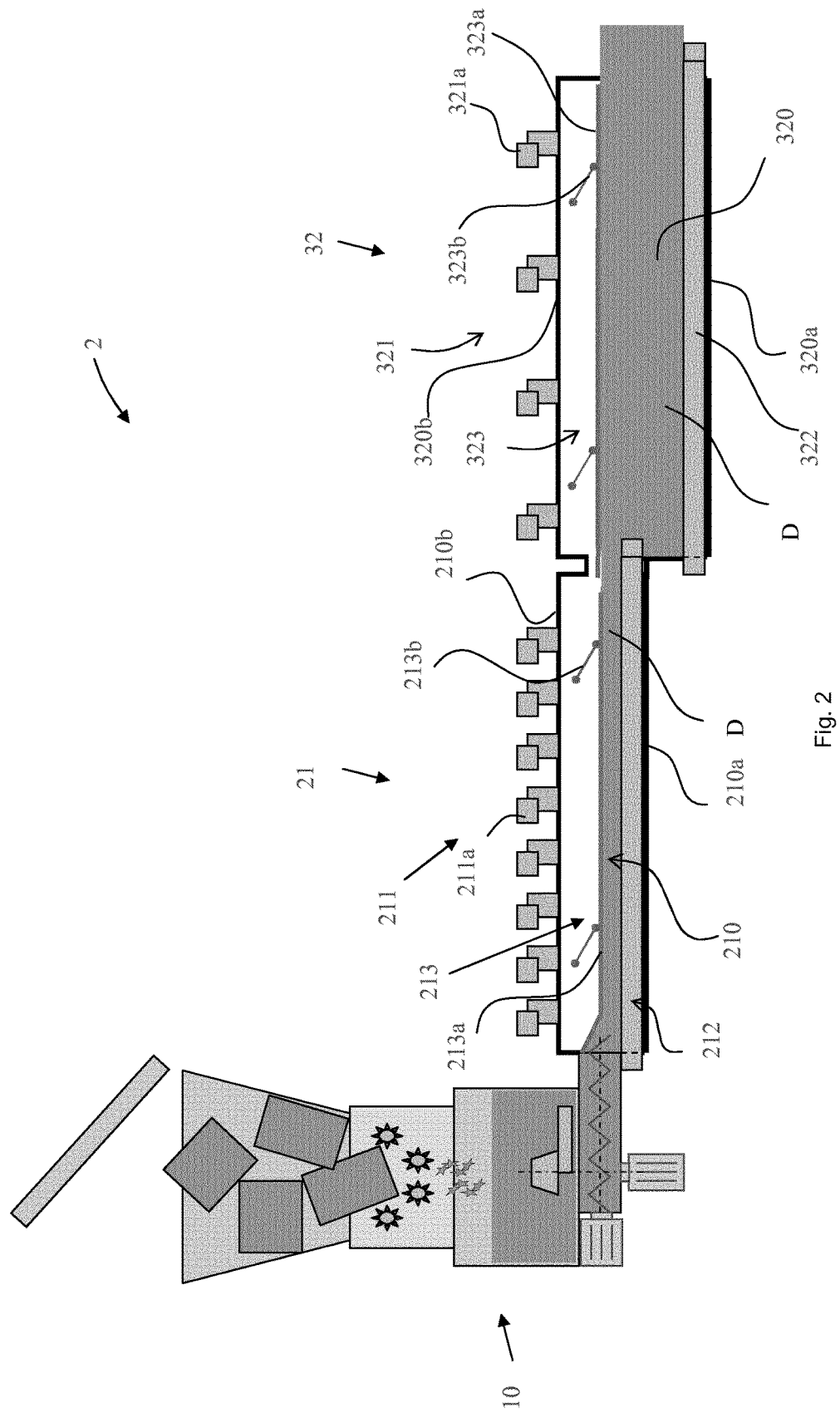
Figure 3:
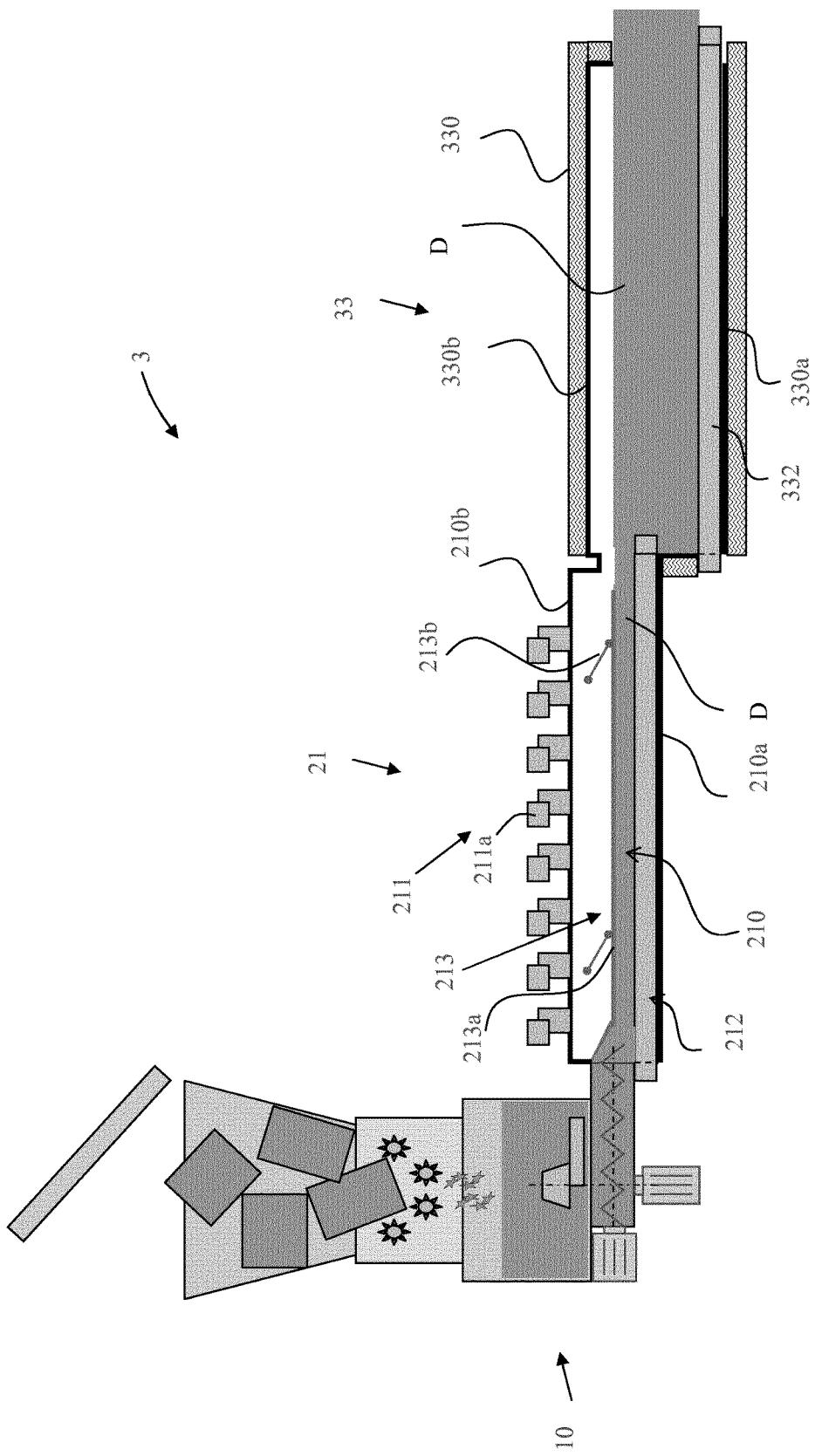
Figure 7:
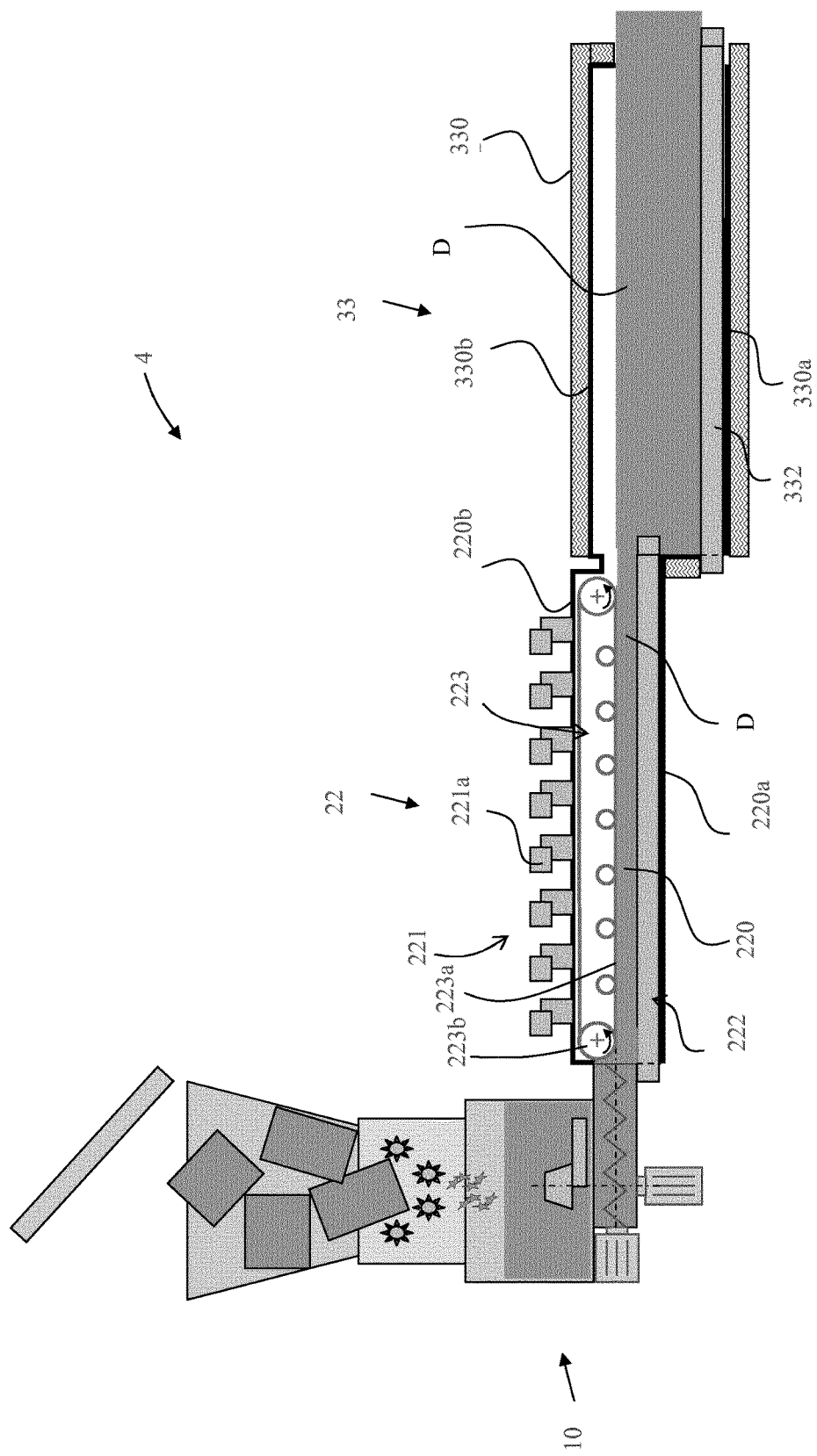

FIG. 2 is a view of a facility according to the invention according to a second embodiment, comprising a system according to the invention as the second system for raising the temperature of the products and a further system according to the invention as the third system for holding the temperature of the products, FIG. 3 is a view of a facility according to the invention according to a third embodiment, comprising a system according to the invention as the second system for raising the temperature of the products and a third system for holding the temperature of the products, FIG. 4 is a view, along a vertical cross-section, of a system according to the invention, FIGS. 5*a* to 5*e* illustrate the various stages of a feed cycle of the moving floor transportation device, FIG. 6 is a detailed, cross-sectional, view of three consecutive slats of a moving floor which may be used according to the invention, FIG. 7 is a view of a facility according to FIG. 3 wherein the suspended confinement plate type confinement device is replaced by a belt conveyor type confinement device.

In addition, the invention relates to a system for the continuous treatment of products by thermal input, comprising:
  a product treatment chamber 210; 220; 320,
  a device 211; 221; 321 for supplying heat by microwave generators 211*a*; 221*a*; 321*a*, arranged with respect to said chamber 210; 220; 320 such that the microwaves are contained in said chamber,
  a moving floor transportation device 212; 222; 322, resting on the bottom of the chamber 210; 220; 320, capable of transporting a layer of products from the entry thereof into the chamber until the exit thereof from the chamber, a confinement device 213; 223; 323 for the waste and the vapours released thereby, inside said chamber.

The treatment chamber is defined between a bottom 210*a*; 220*a*; 320*a*, a cover 210*b*; 220*b*; 320*b*, and side walls connecting the bottom 210*a*; 220*a*; 320*a* to the cover 210*b*; 220*b*; 320*b*. The bottom wall, the cover walls and the side walls are made of a microwave-impermeable material so as to contain the microwaves inside the chamber.

Preferably, the bottom 210*a*; 220*a*; 320*a*, the cover 210*b*; 220*b*; 320*b* and the side walls form a tunnel, particularly having a rectangular cross-section, extending from the entry of the products into the chamber to the exit thereof from the chamber.

The device 211; 221; 321 for supplying heat comprises at least one microwave generator 211*a*; 221*a*; 321*a*. These microwave generators are situated outside the chamber 210; 220; 320, and preferably above the cover 210*b*; 220*b*; 320*b*. To this end, the cover wall has, adjacent to the generators, local microwave-permeable zones.

The moving floor transportation device 212; 222; 322, resting on the bottom of the chamber 210; 220; 320, is capable of transporting a layer of products D, from the entry thereof into the chamber until the exit thereof from the chamber. Such a transportation device, known per se from the prior art, conventionally comprises a set of slats arranged in parallel and forming said floor, along with a system for controlling the slats according to an alternating movement. Such a moving floor transportation device, also usually referred to a "moving bottom", is however not known from the prior art of the field of the invention, i.e. that of continuous microwave treatment devices, in particular those used for the decontamination or hygienisation of waste, but merely from the specific field of semi-trailers. Such moving bottoms are then used for unloading bulk products from the semi-trailer body.

The set of slats of such a floor is typically formed from at least three slat subassemblies, referenced 212*a*; 212*b*; 212*c*, respectively, and each comprising at least N slats, N being a positive integer. The N slats of each subassembly may be moved jointly, independently from the N slats of the other subassemblies. Each slat of a subassembly is separated from the adjacent one of the same subassembly by at least two slats each belonging to one of the other subassemblies.

The feed cycle implemented by the control system for a moving floor comprising, by way of example, three slat subassemblies, as well as the various stages thereof are illustrated in FIGS. 5*a* to 5*e*.

In FIG. 5*a*, the slats of the three subassemblies 212*a*, 212*b* and 212*c* are aligned. The control system actuates, in a first step, the slats of the subassembly 212*a*, in reverse, to the position illustrated in FIG. 5*b*, whereas the slats of the two other subassemblies 212*b* and 212*c* remain stationary. During this action, the materials resting on the floor do not move, the slats of the subassembly 212*a* sliding under the products.

The control system actuates, in a second step, the slats of the subassembly 212*b* in reverse to the position illustrated in FIG. 5*c* whereas the slats of the two other subassemblies 212*a* and 212*c* remain stationary. During this action, the products resting on the floor do not move, the slats of the subassembly 212*b* sliding under the products.

The control system actuates, in a third step, the slats of the subassembly 212*c* in reverse to the position illustrated in FIG. 5*d* whereas the slats of the two other subassemblies 212*a* and 212*b* remain stationary. During this action, the products resting on the floor do not move, the slats of the subassembly 212*c* sliding under the products.

Finally, in a fourth step, the set of slats of the various subassemblies 212*a*, 212*b*, 212*c* are actuated simultaneously forwards, causing the feed of the products by one step. The cycle described in four steps is repeated in order to move the waste forwards step by step.

The adjacent movable slats, belonging to each slat subassembly 212*a*, 212*b*, 212*c* of the moving floor may not be joined as illustrated in FIG. 6, but, on the other hand, be separated from one another according to a configuration known per se from the prior art of moving floors. In particular, lower, fixed, guiding elements 212*d*, having a U-shaped cross-section, may carry out the translational guidance of the slats belonging to each subassembly 212*a*, 212*b*, 212*c* in turn having an inverted U-shaped cross-section and positioned overlapping on the ends of two juxtaposed guiding elements 212*d*, by means of a seal 212*e*. Such a moving floor configuration further provides satisfactory liquid-tightness.

The confinement device 213; 223; 323 of the products and vapours released thereby is inside said chamber 210; 220; 320 and is microwave-permeable. It is arranged between the layer of products D and the microwave generators 211*a*; 221*a*; 321*a*. The function of this device is that of locally containing the products and vapours released thereby, in a reduced volume of said chamber.

Such a confinement device 231; 223; 323 advantageously makes it possible to enhance the thermal performances in the treatment chamber, by limiting heat losses between the layer of products and the atmosphere present in the chamber. Such a confinement device makes it possible to raise the products to higher temperatures or at the very least increase the energy efficiency of the system.

According to one embodiment, the confinement device comprises a confinement plate 213*a*; 323*a*, inside said chamber 210; 320 intended to bear on the top of the layer of products D. This confinement plate is impermeable to vapours, but is made of a microwave-permeable material (i.e. polytetrafluoroethylene: PTFE), so as to be traversed thereby. This confinement plate 231*a*; 323*a* is preferably substantially parallel to the moving floor and is preferably movable with respect to a fixed portion of the facility via suspension means such as rocking levers 231*b*; 323*b*.

As seen in FIG. 5, this plate 213*a*; 323*a* extends in width from one side wall to the other side wall of the chamber, and in length, in the vicinity of the entry of the products into the chamber and to in the vicinity of the exit thereof from the chamber. The layer of products D as well as the vapours released thereby are then contained in the confinement device between the floor, the underside of the confinement plate 231*a*; 323*a* and the sections of the side walls extending between the confinement plate and the floor.

The means for suspending the confinement plate 213*a*; 323*a* from said fixed portion may be rocking levers 213*b*; 323*b* or equivalent, passive, mechanisms, enabling the confinement plate to rest under its own weight on the layer of products D, while allowing same to be raised as the products move forwards, under the action of the moving floor. By bearing on the top of the layer of products preferably under the action of its own weight, the confinement plate advantageously makes is possible to maintain a uniform thickness of the layer of products.

Alternatively, and according to an embodiment illustrated in FIG. 7, the confinement device 223 of the products and vapours released thereby comprises a belt conveyor, inside said chamber 220, said belt conveyor comprising a flexible belt 223a, guided by rotary guiding cylinders 223b, said flexible belt 223a being intended to bear on the layer of products D. The belt conveyor is arranged in said chamber 220 between, on one hand, the microwave generators 221a of said device 221 for supplying heat by microwave generators and, on the other, the layer of products D, said flexible belt 223a being intended to be traversed by the microwaves and being made of a microwave-permeable material such as silicone.

The function of this belt conveyor is that of confining the products and vapours in a defined volume between the belt conveyor, and the sections of the side walls between the belt and the moving floor. The guiding cylinders 223b, free in rotation, enable the flexible belt 223a to move forwards, under the action of the layer of products D, at each feed triggered by the moving floor and so as not to impede the progression of the products.

In both cases whether in the case of the movable confinement plate confinement device, or the belt conveyor confinement device, the confinement device forms a physical cover bearing on the layer of products, advantageously without this cover impeding the progression of the products by the action of the moving floor, and without any empty space between the layer of product and the confinement device, and as seen in FIG. 1 of the document DE 35 05 570C1.

According to one embodiment, the system may allow an additional thermal input via the moving floor which may be heated directly by any known, particularly resistive, means.

The invention also relates to a facility 1; 2; 3; 4 for the continuous treatment of products, comprises, in series:
  a first system 10 for shredding or mixing products, and
  a second system 21; 22 for the continuous treatment of products by thermal input to raise the temperature of the products,
  a third system 31; 32; 33 for holding the temperature of the products.

According to the invention, the second system or the third system essentially consists of a system for the continuous treatment of products, according to the invention. Optionally, the second system and the third system each consist essentially of such a system according to the invention.

The first system 10 may comprise a hopper, followed by means for shredding the products in aggregate form, or means for mixing the aggregates. The second system 21; 22 essentially consists of a system according to the invention.

The entry of the treatment chamber 210; 220 of the second system 21; 22 may be fed by one or a plurality of screw conveyors, so as to form a layer of products, in the chamber 210; 220, particularly between the confinement plate 213a and the moving floor transportation device 212, as illustrated in FIG. 1 to 3, or between the flexible belt 223a of the belt conveyor and the moving floor transportation device 222 as illustrated in FIG. 7.

The system for controlling the moving floor makes it possible to move the layer of products from the entry thereof into the chamber up to the exit thereof from the chamber from which the products are conveyed, preferably gravitationally, until the entry of the third system 31; 32; 33 intended to hold the temperature of the waste.

In the treatment chamber 210; 220 of the second system, the temperature of the products is rapidly raised by the microwaves, or also by an additional thermal input from the moving floor. In the case of a treatment for the decontamination of waste having an infectious risk, the second system makes it possible to raise the temperature of the waste above 100° C., in the region of 100° C. for example between 100° C. and 110° C. In the case of waste hygienisation, the second system makes it possible to raise the temperature of the waste above 70° C., for example between 70° C. and 75° C.

The third system 31; 32; 33 intended for holding the temperature of the products enables holding at a similar temperature, but greater than that of the products leaving the second system, for example by over 5° C.

This third system may have various forms. According to a first embodiment, particularly illustrated in FIG. 1, this third system may comprise a heated tank 311, inside which an endless screw 312 rotates, which moves the products in this third system 31. The endless screw 312 is driven by the motor 313.

According to a second embodiment, particularly illustrated in FIG. 2, the third system may consist essentially of a system according to the invention, comprising:
  a treatment chamber 320, formed between a cover 320b, a bottom 320a and side walls,
  a device 321 for supplying heat by microwave generators 321a, the generators being arranged outside the chamber, above the cover 320b such that the microwaves are contained in said chamber,
  a moving floor transportation device 322, resting on the bottom of the chamber 320, capable of transporting a layer of products D, from the entry thereof into the chamber until the exit thereof from the chamber,
  a confinement device 323 of the products and vapours released thereby, inside said chamber, comprising a movable confinement plate 323a, bearing on the products and suspended with respect to a fixed portion of the facility, by a system of rocking levers such as 323b.

According to a third embodiment, particularly illustrated in FIG. 3 or in FIG. 7, the third system 33 comprises a chamber 330 formed between a cover 330b, a bottom 330a, and side walls forming a tunnel, as well as a moving floor 332 resting on the bottom 330a. In this chamber, the products are held at a temperature by heating the walls, for example by means of resistive heating.

Naturally, further embodiments could be envisaged by those skilled in the art without leaving the scope of the invention defined by the claims hereinafter.

NOMENCLATURE 1, 2, 3, 4. Facility for the continuous treatment of products,
10. First system for shredding or mixing products,
21, 22. Second system for the continuous treatment of products by thermal input for raising the temperature of the products,
31, 32, 33. Third system for holding the temperature of the products,
210, 220, 320, 330 Product treatment chamber,
211, 221, 321. Device for supplying heat by microwave generators,
212, 222, 322, 332. Moving floor transportation device,
213, 223, 323. Confinement device of products and vapours, inside the chamber.
311. Heated tank,
312. Endless screw,
313. Motor,
D. Layer of waste
210a, 220a, 320a, 330a. Bottom,
210b, 220b, 320b, 330b. Cover,
211a, 221a, 321a. Microwave generators,
212a. First slat subassembly, 212*b*. Second slat subassembly,
212*c*. Third slat subassembly,
212*d*. Slat guiding elements, having a U-shaped cross-section,
212*e*. Seals,
213*a*, 323*a*. Confinement plate,
213*b*, 323*b*. Rocking lever system,
223*a*. Flexible belt of belt conveyor,
223*b*. Belt conveyor guiding cylinders.

The invention claimed is:

1. System (21; 22; 32) for the continuous treatment of waste by thermal input, for the hygienisation of waste or the decontamination of waste having an infectious risk, comprising:
 a waste treatment chamber (210; 220; 320),
 a device (211; 212; 321) for supplying heat by microwave generators (211*a*; 221*a*; 321*a*), arranged with respect to said chamber (210; 220; 320) such that the microwaves are contained in said chamber (210; 220; 320),
 a moving floor transportation device (212; 222; 322), resting on the bottom of the chamber (210; 220; 320), comprising a set of slats arranged in parallel and forming said floor, along with a system for controlling the slats according to an alternating movement, capable of transporting a layer of waste (D) from the entry thereof into the chamber until the exit thereof from the chamber,
 a confinement device (213; 223; 323) for the waste and the vapours released thereby, inside said chamber.

2. System according to claim 1, wherein said confinement devices (213; 323) of the waste and the vapours released thereby comprises a confinement plate (213*a*; 323*a*), inside said chamber (210; 320), intended to bear on the top of the layer of waste (D), movable with respect to a fixed portion of the system via passive suspension means, enabling the confinement plate (213*a*; 323*a*) to rest under its own weight on the layer of products (D), while allowing same to be raised as the products move forwards, under the action of the moving floor transportation device.

3. System according to claim 2, wherein the confinement plate (213*a*; 323*a*) is arranged in said chamber (210; 320) between, on one hand, the microwave generators (211*a*; 321*a*) of said device (211; 321) for supplying heat by microwave generators and, on the other, the layer of waste (D), said confinement plate (213*a*; 323*a*) being intended to be traversed by the microwaves and being made of a microwave-permeable material.

4. System according to claim 2, wherein said confinement plate (213*a*; 323*a*) is suspended from the fixed portion of the facility by a system of rocking levers (213*b*; 323*b*).

5. System according to claim 1, wherein the confinement device (223) of the waste and vapours released thereby comprises a belt conveyor, inside said chamber (220), said belt conveyor comprising a flexible belt (223*a*), guided by rotary guiding cylinders (223*b*), said flexible belt (223*a*) being intended to bear on the layer of waste (D).

6. System according to claim 5, wherein the belt conveyor is arranged in said chamber (220) between, on one hand, the microwave generators (221*a*) of said device (221) for supplying heat by microwave generators and, on the other, the layer of waste (D), said flexible belt (223*a*) being intended to be traversed by the microwaves and being made of a microwave-permeable material such as silicone.

7. System according to claim 1, wherein the moving floor transportation device (212; 222; 322) is formed from said set of slats consisting of at least three subassemblies (212*a*, 212*b*, 212*c*), said slats being arranged in parallel, along with a system for the sequential control of the slats according to an alternating movement.

8. System according to claim 7, comprising a device for heating the set of slats so as to form a heating moving floor.

9. Facility (1; 2; 3; 4) for the continuous treatment of waste, comprising, in series:
 a first system (10) for shredding or mixing waste,
 a second system (21; 22) for the continuous treatment of waste by thermal input to raise the temperature of the waste,
 a third system (31; 32; 33) for holding the temperature of the waste,
 and wherein said second system consists of a system according to claim 1.

10. Facility (1; 2; 3; 4) for the continuous treatment of waste, comprising, in series:
 a first system (10) for shredding or mixing waste,
 a second system (21; 22) for the continuous treatment of waste by thermal input to raise the temperature of the waste,
 a third system (32) for holding the temperature of the waste and wherein said third system consists of a system according to claim 1.

11. A method for the hygienisation of waste comprising:
 providing the system of claim 1; and
 providing waste as input to the system to hygienize the waste.

12. A method for the decontamination of waste having an infectious risk such as medical waste, comprising:
 providing the system of claim 1; and
 providing the waste having an infectious risk as input to the system to decontaminate the waste.

13. System according to claim 3, wherein said confinement plate (213*a*; 323*a*) is suspended from the fixed portion of the facility by a system of rocking levers (213*b*; 323*b*).

14. System according to claim 2, wherein the moving floor transportation device (212; 222; 322) is formed from said set of slats consisting of at least three subassemblies (212*a*, 212*b*, 212*c*), said slats being arranged in parallel, along with a system for the sequential control of the slats according to an alternating movement.

15. System according to claim 3, wherein the moving floor transportation device (212; 222; 322) is formed from said set of slats consisting of at least three subassemblies (212*a*, 212*b*, 212*c*), said slats being arranged in parallel, along with a system for the sequential control of the slats according to an alternating movement.

16. System according to claim 4, wherein the moving floor transportation device (212; 222; 322) is formed from said set of slats consisting of at least three subassemblies (212*a*, 212*b*, 212*c*), said slats being arranged in parallel, along with a system for the sequential control of the slats according to an alternating movement.

17. System according to claim 5, wherein the moving floor transportation device (212; 222; 322) is formed from said set of slats consisting of at least three subassemblies (212*a*, 212*b*, 212*c*), said slats being arranged in parallel, along with a system for the sequential control of the slats according to an alternating movement.

18. System according to claim 6, wherein the moving floor transportation device (212; 222; 322) is formed from said set of slats consisting of at least three subassemblies (212*a*, 212*b*, 212*c*), said slats being arranged in parallel, along with a system for the sequential control of the slats according to an alternating movement.

19. Facility (1; 2; 3; 4) for the continuous treatment of waste, comprising, in series:
- a first system (10) for shredding or mixing waste,
- a second system (21; 22) for the continuous treatment of waste by thermal input to raise the temperature of the waste,
- a third system (31; 32; 33) for holding the temperature of the waste, and wherein said second system consists of a system according to claim 2.

20. Facility (1; 2; 3; 4) for the continuous treatment of waste, comprising, in series:
- a first system (10) for shredding or mixing waste,
- a second system (21; 22) for the continuous treatment of waste by thermal input to raise the temperature of the waste,
- a third system (31; 32; 33) for holding the temperature of the waste, and wherein said second system consists of a system according to claim 3.

* * * * *